(12) United States Patent
Zhang et al.

(10) Patent No.: US 8,871,930 B2
(45) Date of Patent: Oct. 28, 2014

(54) PREPARATION METHOD OF ALPHA-IMATINIB MESYLATE

(75) Inventors: Xinyu Zhang, Zhejiang (CN); Jiankang Xu, Zhejiang (CN)

(73) Assignee: Zhejiang Jiuzhou Pharma Science & Technology Co., Ltd., Hangzhou, Zhejiang (CN)

( * ) Notice: Subject to any disclaimer, the term of this patent is extended or adjusted under 35 U.S.C. 154(b) by 0 days.

(21) Appl. No.: 13/989,643

(22) PCT Filed: Nov. 16, 2011

(86) PCT No.: PCT/CN2011/082267
§ 371 (c)(1),
(2), (4) Date: May 24, 2013

(87) PCT Pub. No.: WO2012/071980
PCT Pub. Date: Jun. 7, 2012

(65) Prior Publication Data
US 2013/0245258 A1   Sep. 19, 2013

(30) Foreign Application Priority Data
Nov. 30, 2010 (CN) .......................... 201010567773

(51) Int. Cl.
| | | |
|---|---|---|
| *C07D 401/00* | (2006.01) |
| *C07D 403/00* | (2006.01) |
| *C07D 405/00* | (2006.01) |
| *C07D 409/00* | (2006.01) |
| *C07D 411/00* | (2006.01) |
| *C07D 413/00* | (2006.01) |
| *C07D 417/00* | (2006.01) |
| *C07D 419/00* | (2006.01) |
| *C07D 401/14* | (2006.01) |
| *C07D 401/04* | (2006.01) |

(52) U.S. Cl.
CPC ............ *C07D 401/14* (2013.01); *C07D 401/04* (2013.01)

USPC .......................................... 544/331

(58) Field of Classification Search
USPC .......................................... 544/331; 514/275
See application file for complete search history.

(56) References Cited

U.S. PATENT DOCUMENTS

| 5,521,184 A | 5/1996 | Zimmermann | |
| 2006/0223816 A1* | 10/2006 | Adin et al. | ............... 514/252.18 |
| 2007/0265288 A1* | 11/2007 | Pathi et al. | ................... 514/275 |

FOREIGN PATENT DOCUMENTS

| WO | WO 99/03854 | 1/1999 |
| WO | WO 2004/106326 | 12/2004 |
| WO | WO 2005/077933 | 8/2005 |
| WO | WO 2006/024863 | 3/2006 |
| WO | WO 2006/054314 | 5/2006 |
| WO | WO 2007/023182 | 3/2007 |
| WO | WO 2007/136510 | 11/2007 |
| WO | WO 2009/151899 | 12/2009 |
| WO | WO 2010/133976 | 1/2010 |

OTHER PUBLICATIONS

N.G. Anderson, Practical Process & Research Development 81-111, 114-143, (2000).*
International Search Report from International Application No. PCT/CN2011/082267 mailed Feb. 23, 2013.
Office Action from Chinese Application No. 201010567773.X issued Nov. 8, 2013.
International Search Repot from European Application No. EP 1 184 491 6.4 mailed Mar. 7, 2014.

\* cited by examiner

*Primary Examiner* — James O Wilson
*Assistant Examiner* — Alexander R Pagano
(74) *Attorney, Agent, or Firm* — Merchant & Gould P.C.

(57) ABSTRACT

Disclosed is a preparation method of α-imatinib mesylate. The reaction temperature of the method is low and the yield of the crystal is improved. Furthermore, the method is applicable to the industrial production.

8 Claims, 2 Drawing Sheets

PREPARATION METHOD OF ALPHA-IMATINIB MESYLATE

This application is a National Stage Application of PCT/CN2011/082267, filed 16 Nov. 2011, which claims benefit of China Patent Application No. 201010567773.x, filed with the Patent Office of China on Nov. 30, 2010, titled "Preparation method of α-imatinib mesylate", which application) are incorporated herein by reference. To the extent appropriate, a claim of priority is made to each of the above disclosed applications.

FIELD OF THE INVENTION

The present invention relates to the field of pharmaceutical synthesis, particularly to a method for preparing α-crystal form of imatinib mesylate.

BACKGROUND OF THE INVENTION

Imatinib mesylate, chemical name: 4-[(4-methyl-1-piperazinyl)methyl]-N-[4-methyl-3-[[4-(3-pyridinyl)-2-pyrimidinyl]amino]phenyl]-benzamide methanesulfonate, molecular formula: $C_{29}H_{31}N_7O \cdot CH_4SO_3$, molecular weight: 589.7, the structural formula is as follows:

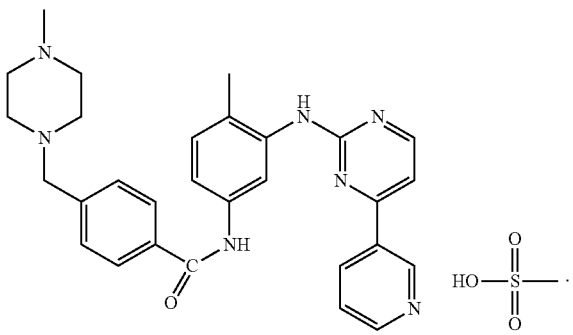

Imatinib mesylate, an inhibitor of signal transduction, was developed by Novartis (Switzerland), and was initially marketed in the United States on May 10, 2001. Currently, it has been marketed in more than 60 countries including the United States, the European Union, Japan, and China.

Studies have found that imatinib mesylate can inhibit Bcr-Abl tyrosine kinase at cellular level both in vivo and in vitro, and can selectively inhibit the proliferation of, and induce the apoptosis of cells of Bcr-Abl positive cell lines, as well as fresh cells from patients of Philadelphia chromosome-positive chronic myelocytic leukemia and acute lymphocytic leukemia. In addition, it can also inhibit the tyrosine kinases of the receptor of platelet-derived growth factor (PDGF) and c-Kit, the receptor of stem cell factor (SCF), thus inhibit PDGF- and SCF-mediated cellular events. Imatinib mesylate, which belongs to small-molecule targeted anticancer drug, is suitable for the treatment of patients having chronic myelocytic leukemia (CML) in blast phase, accelerated phase, or in chronic phase after failure of interferon-alpha treatment, as well as patients having unresectable or metastatic malignant gastrointestinal stromal tumors (GIST).

Imatinib and the salt form thereof are first described in U.S. Pat. No. 5,521,184. International Patent Application WO99/03854, WO2005/077933, WO2004/106326, WO2006/054314 and WO2007/023182 have disclosed α, β, α2, H1, I, II, δ, and ε crystal forms of imatinib mesylate. US Patent Application US20060223816 provides a method for preparing α-crystal form of imatinib mesylate, which is stable, well flowable, and suitable for pharmaceutical application. Specifically, mixing the imatinib base with organic solvents, and heating until some of the imatinib base being dissolved in the organic solvents; adding seed crystal of α-crystal form of imatinib mesylate; dissolving methanesulfonic acid in organic solvents, then slowly adding it dropwise into the solution of imatinib base; cooling the reaction liquid to allow the precipitation of imatinib mesylate crystal, separating to obtain the α-crystal form of imatinib mesylate. The organic solvents in this patent application are ketones including butanone and methyl isobutyl ketone. The reaction temperature is relatively high, while the imatinib base is sensitive to heat, and is susceptible to thermal degradation, which leads to a low product yield of only 85%~90%.

SUMMARY OF THE INVENTION

The purpose of the present invention is to provide a high yield method for the preparation of α-crystal form of imatinib mesylate.

To achieve the purpose of the present invention, the present invention employs the following technical solutions:

A method for preparing α-crystal form of imatinib mesylate is that imatinib base is mixed with acetone, then reacted with methanesulfonic acid at 20~60° C. to obtain the α-crystal form of imatinib mesylate.

The equation is as follows:

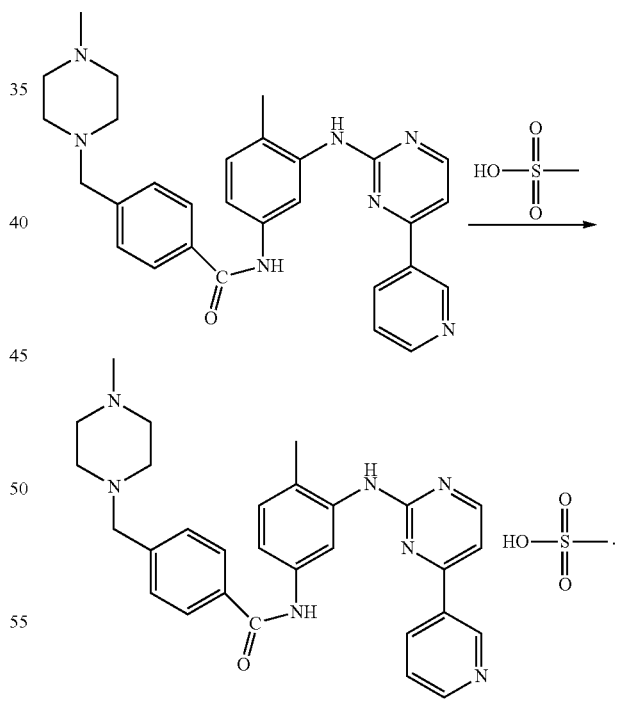

A suspension is formed after mixing imatinib base with acetone, so that the imatinib base is dispersed homogeneously, and is reacted with methanesulfonic acid completely. Imatinib base has different solubilities in three solvents, acetone, butanone and methyl isobutyl ketone, of which the solubility of imatinib base in acetone is extremely low in comparison with those in butanone and methyl isobutyl ketone. Imatinib base can dissolve by refluxing at 75° C.

using 50-fold mass of butanone as solvent, and can dissolve as well by reacting at 100~110° C. using 80-fold mass of methyl isobutyl ketone as solvent, but can hardly dissolve by refluxing at 57° C. using 165-fold mass of acetone as solvent, and can dissolve, but can not form a clarified solution, by refluxing at 57° C. using 250-fold mass of acetone as solvent. Due to the extremely low solubility of imatinib base in acetone, the imatinib base is mixed with acetone in the preparation method according to the present invention to form a suspension, which reduces the loss of raw material of imatinib base caused by the substantial dissolution of imatinib base in solvents, thus improving the yield.

In another aspect, the three solvents, acetone, butanone and methyl isobutyl ketone, have different boiling points, the boiling point of butanone is 79.6° C., the boiling point of methyl isobutyl ketone is 115.8° C., and the boiling point of acetone is only 56.48° C., which is significantly lower than those of butanone and methyl isobutyl ketone. Therefore, using acetone as solvent can reduce the reaction temperature, so as to reduce the thermal degradation loss of imatinib base, thus improving the yield.

The preparation method according to the present invention is carried out at 20~60° C.

As a preference of the preparation method according to the present invention, the mass ratio of imatinib base to acetone is 1:10~100. More preferably, the mass ratio of imatinib base to acetone is 1:15~30.

In a preferred embodiment of the preparation method according to the present invention, the molar ratio of imatinib base to methanesulfonic acid is 1:1.0~1.5. More preferably, the molar ratio of imatinib base to methanesulfonic acid is 1:1.

As a preference of the preparation method according to the present invention, the reaction time is 1~36 h. More preferably, the reaction time is 4~10 h.

Since methanesulfonic acid is a colorless or light brown oily liquid at room temperature, and is very viscous, it is diluted by mixing with organic solvents, allowing more complete reaction of imatinib base with methanesulfonic acid. In addition, the solubility of imatinib base in acetone is low, and the thermal degradation loss is little. Therefore, in a preferred embodiment, a mixed liquid is formed by mixing methanesulfonic acid with acetone first, which is then reacted with a mixed liquid of imatinib base and acetone.

As a preference, the mass ratio of imatinib base to acetone is 1:15~20. More preferably, the mass ratio of imatinib base to acetone is 1:15.

Seed crystal is an insoluble additive which is added to form a crystal nucleus during the crystallization process. The seed crystal can accelerate or promote the growth of the enantiomeric crystal having the same crystal form or spatial configuration as the seed crystal.

In a preferred embodiment, the preparation method according to the present invention further comprises adding the seed crystal of α-crystal form of imatinib mesylate. As a preference, the mass ratio of the seed crystal of α-crystal form of imatinib mesylate to the imatinib base is 1:300~1000.

The preparation method according to the present invention further comprises filtering, washing, and drying the obtained α-crystal form of imatinib mesylate.

Wherein, the filtering is carried out after being cooled to 20~25° C. under the protection of nitrogen gas. Nitrogen gas is commonly used as a protective gas for its stable chemical properties of not easily reacting with other substances.

In the preparation method according to the present invention, the washing is preferably rinsing with acetone.

As a preference, the drying is carried out at 60° C. In the preparation method according to the present invention, acetone is used as solvent in order to reduce the loss of raw material of imatinib base. The boiling point of acetone is 56.48° C., and vaporization of acetone at 60° C. can remove the solvent in the α-crystal form of imatinib mesylate, thus improving the purity of the product. More preferably, the drying is carried out at 60° C. under vacuum.

According to the nature that specific polymorph can produce disparate spectra, the product of prepared by the preparation method according to the present invention is determined to be the α-crystal form of imatinib mesylate by powder X-ray diffraction (XRPD), and the melting point of the crystal is determined by differential scanning calorimetry (DSC).

The preparation method according to the present invention is carried out at lower reaction temperature, which greatly reduces the degradation of imatinib, thus improving the yield. Experiments show that the product yield of the α-crystal form of imatinib mesylate prepared by the preparation method according to the present invention is greater than 97%. The process of the present invention is highly stable, simple to operate, low in cost, and can obtain highly pure α-crystal form of imatinib mesylate, and is suitable for the industrialized production of α-crystal form of imatinib mesylate, and has very high economic benefits.

DETAILED EMBODIMENTS

The present invention discloses a method for preparing α-crystal form of imatinib mesylate. A skilled in the art can learn from the contents herein, and achieve by appropriately improving the process parameters. Specifically, all the similar alterations and changes are obvious to a skilled in the art, and are deemed to be within the scope of the present invention. The method according to the present invention has been described with reference to preferred examples, and the method described herein can obviously be modified or appropriately changed and combined by related personnel without departing from the contents, spirit, and scope of the present invention, to achieve and apply the techniques of the present invention.

In order to further understand the present invention, the method for preparing α-crystal form of imatinib mesylate provided by the present invention is illustrated in detail, in conjunction with examples. It should be understood that these descriptions are intend to further illustrate the characteristics and advantages of the present invention, rather than to limit the claims of the present invention.

EXAMPLE 1

Figure 1:
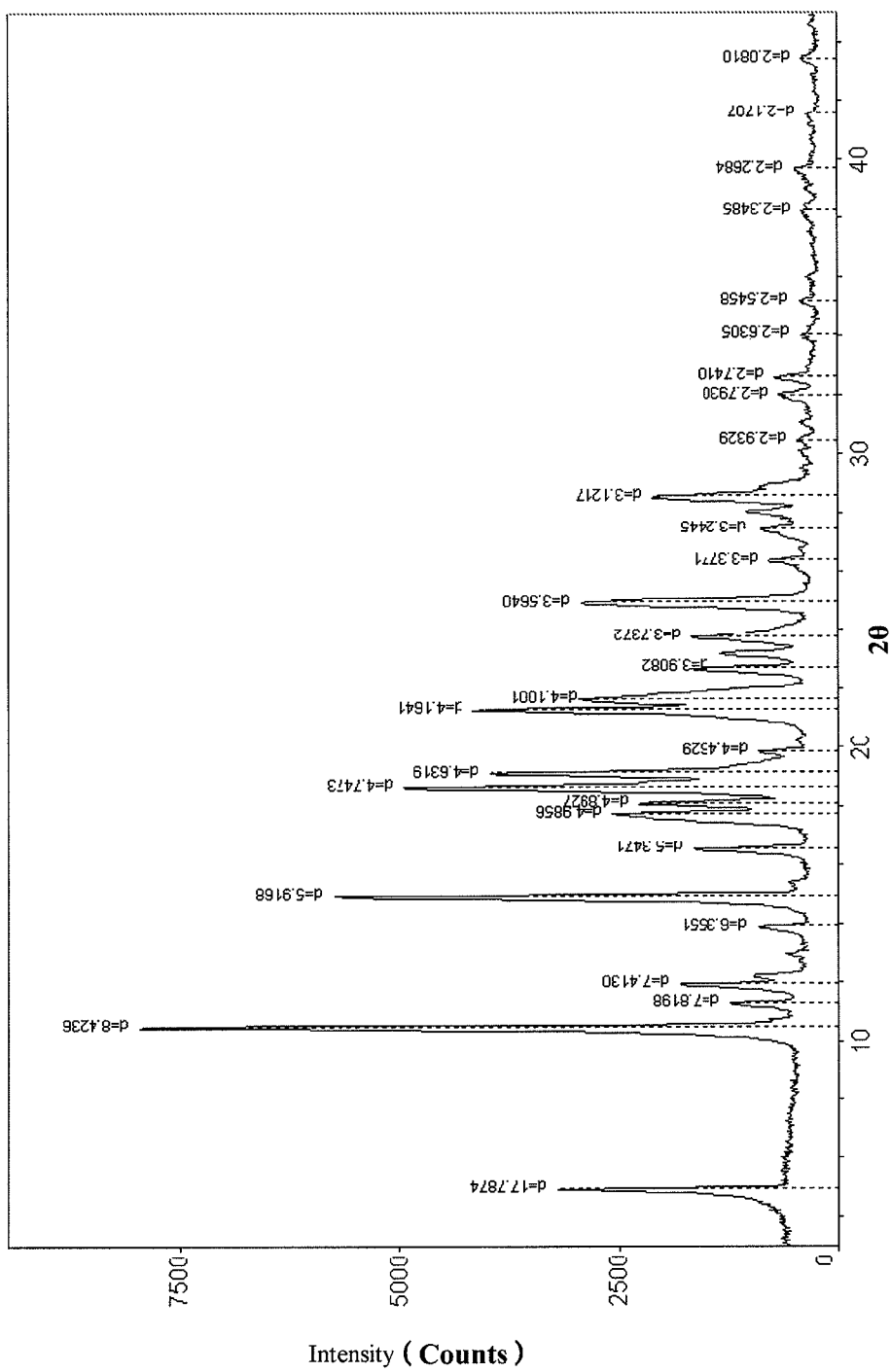
FIG. 1 illustrates the spectrum of powder X-ray diffraction of the α-crystal form of imatinib mesylate prepared in accordance with Example 1 of the present invention.
Figure 2:
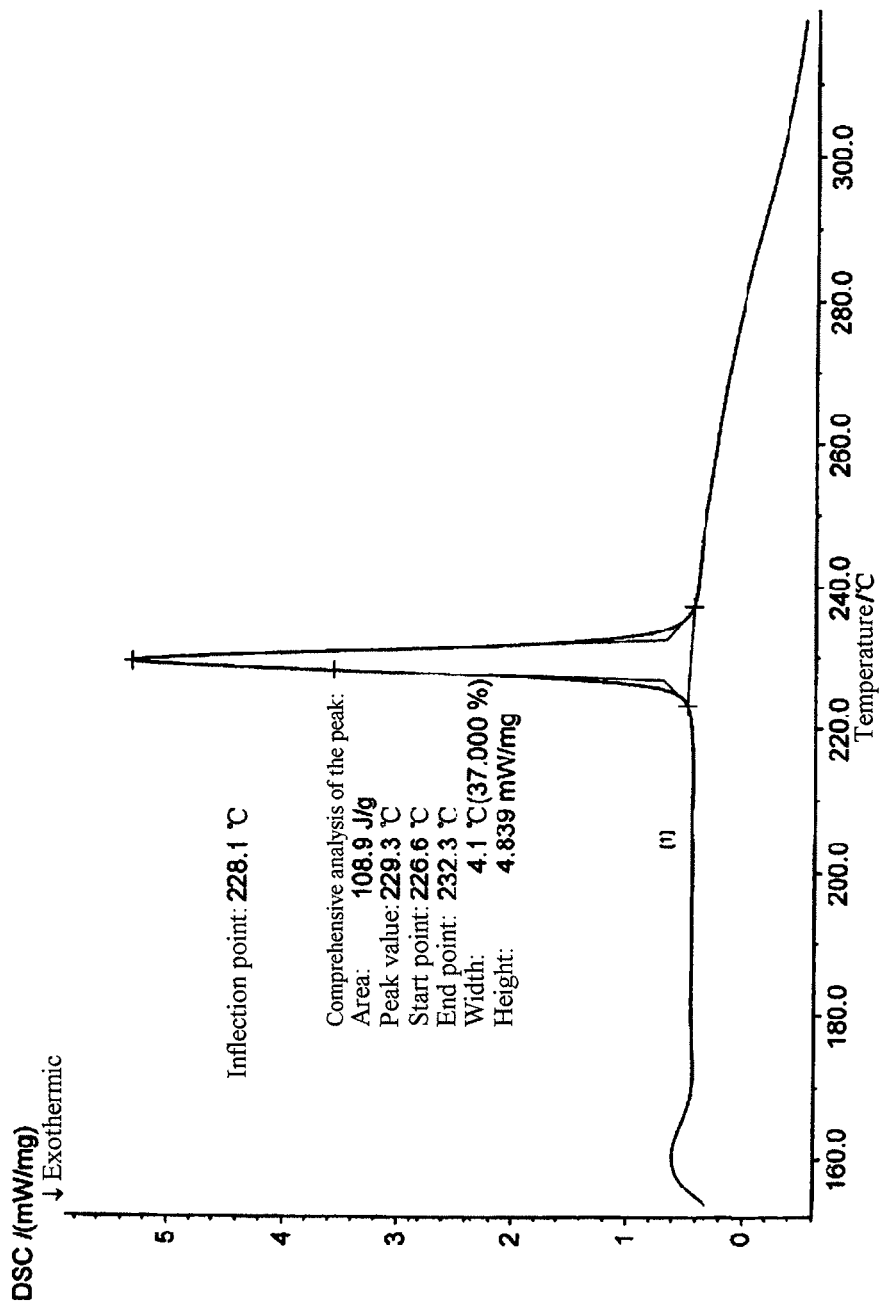
FIG. 2 illustrates the DSC spectrum of the α-crystal form of imatinib mesylate prepared in accordance with Example 1 of the present invention.

To a 500 mL four-neck reaction flask, 30 g (60.77 mmol) imatinib base, 300 g acetone, and 0.1 g crystal seed of the α-crystal form were added, and heated to 55~60° C., and a mixture of 5.84 g (60.77 mmol) methanesulfonic acid and 88.65 g acetone was added dropwise for 2 hour while stirring, then the reaction mixture was cooled to 20~25° C., filtered under the protection of nitrogen gas, rinsed with 50 g acetone, and the filter cake was dried under vacuum at 60° C. for more than 12 hours, to obtain about 35.80 g dry product of the α-crystal form of imatinib mesylate, yield 99.89%, HPLC 99.91%. The prepared α-crystal form of imatinib mesylate was determined by using powder X-ray diffractometry and differential scanning calorimetry (DSC). The XRPD spectrum is shown in FIG. 1, and the angles of reflection (2θ) are about: 4.8, 10.4, 11.2, 11.9, 12.9, 13.8, 14.9, 16.4, 17.0, 18.1, 18.6, 19.0, 19.8, 21.2, 21.6, 22.6, 23.1, 23.7, 24.9, 26.3, 28.5, 31.9, 32.5, 43.4±0.2. The DSC spectrum is shown in FIG. 2, and the peak value is 229° C.

EXAMPLE 2

To a 500 mL four-neck reaction flask, 30 g (60.77 mmol) imatinib base, 450 g acetone, and 0.1 g seed crystal of the α-crystal form were added and heated to 40~45° C., and a mixture of 5.84 g (60.77 mmol) methanesulfonic acid and 116.8 g acetone was added dropwise for 36 hours while stirring, then the reaction mixture was cooled to 20~25° C., filtered under the protection of nitrogen gas, rinsed with 50 g acetone, and the filter cake was dried under vacuum at 60° C. for more than 12 hours, to obtain about 35.20 g dry product of the α-crystal form of imatinib mesylate, yield 98.21%, HPLC 99.70%. The prepared α-crystal form of imatinib mesylate was determined by using powder X-ray diffractometry, the results were the same as Example 1, and the peak value of the spectrum of the differential scanning calorimetry is 227° C.

EXAMPLE 3

To a 500 mL four-neck reaction flask, 30 g (60.77 mmol) imatinib base, 900 g acetone, and 0.1 g seed crystal of the α-crystal form were added, and heated to 20~25° C., and a mixture of 5.84 g (60.77 mmol) methanesulfonic acid and 88.65 g acetone was added dropwise for 4 hours while stirring, then the reaction mixture was filtered under the protection of nitrogen gas, rinsed with 50 g acetone, and the filter cake was dried under vacuum at 60° C. for more than 12 hours, to obtain about 35.00 g dry product of the α-crystal form of imatinib mesylate, yield 97.65%, HPLC 99.85%. The prepared α-crystal form of imatinib mesylate was determined by using powder X-ray diffractometry, the results were the same as example 1, and the peak value of the spectrum of the differential scanning calorimetry is 228° C.

EXAMPLE 4

To a 1000 mL four-neck reaction flask, 30 g (60.77 mmol) imatinib base, 3000 g acetone, and 0.1 g seed crystal of the α-crystal form were added, and heated to 40~45° C., and a mixture of 8.76 g (91.16 mmol) methanesulfonic acid and 160 g acetone was added dropwise for 10 hours while stirring, then the reaction mixture was cooled to 20~25° C., filtered under the protection of nitrogen gas, rinsed with 50 g acetone, and the filter cake was dried under vacuum at 60° C. for more than 12 hours, to obtain about 34.80 g dry product of the α-crystal form of imatinib mesylate, yield 97.10%, HPLC 99.51%. The prepared α-crystal form of imatinib mesylate was determined by using powder X-ray diffractometry, the results were the same as example 1, and the peak value of the spectrum of the differential scanning calorimetry is 229° C.

EXAMPLE 5

To a 500 mL four-neck reaction flask, 30 g (60.77 mmol) imatinib base, and 450 g acetone were added, and heated to 40~45° C., and a solution of 5.84 g (60.77 mmol) methanesulfonic acid was added dropwise for 6 hours while stirring, then the reaction mixture was cooled to 20~25° C., filtered under the protection of nitrogen gas, rinsed with 50 g acetone, and the filter cake was dried under vacuum at 60° C. for more than 12 hours, to obtain about 34.94 g dry product of the α-crystal form of imatinib mesylate, yield 97.5%, HPLC 99.34%. The prepared α-crystal form of imatinib mesylate was determined by using powder X-ray diffractometry, the results were the same as example 1, and the peak value of the spectrum of the differential scanning calorimetry is 227° C.

EXAMPLE 6

To a 500 mL four-neck reaction flask, 30 g (60.77 mmol) imatinib base, and 450 g acetone were added and heated to 50~60° C., a mixture of 5.84 g (60.77 mmol) methanesulfonic acid and 88.65 g acetone was added dropwise for 10 hours while stirring, then the reaction mixture was cooled to 20~25° C., filtered under the protection of nitrogen gas, rinsed with 50 g acetone, and the filter cake was dried under vacuum at 60° C. for more than 12 hours, to obtain about 35.22 g dry product of the α-crystal form of imatinib mesylate, yield 98.27%, HPLC 99.87%. The prepared α-crystal form of imatinib mesylate was determined by using powder X-ray diffractometry, the results were the same as example 1, and the peak value of the spectrum of the differential scanning calorimetry is 228° C.

The illustrations of the above examples are only used to facilitate the understanding of the method according to the present invention, and the core idea thereof. The method for preparing α-crystal form of imatinib mesylate proposed by the present invention has been described by examples, and the method for preparing α-crystal form of imatinib mesylate described herein can obviously be modified or appropriately changed and combined by a related skilled personnel without departing from the contents, spirit, and scope of the present invention, to achieve the techniques of the present invention. Specifically, all the similar alterations and changes are obvious to a skilled in the art, and are deemed to be within the spirit, scope, and contents of the present invention.

The invention claimed is:

1. A method for preparing α-crystal form of imatinib mesylate, characterized in that, imatinib base is mixed with acetone, and heated to 40-60° C., then a mixed solution of methanesulfonic acid and acetone was added dropwise, to obtain the α-crystal form of imatinib mesylate.

2. The preparation method according to claim 1, characterized in that, the mass ratio of imatinib base to acetone is 1:10~100.

3. The preparation method according to claim 2, characterized in that, the mass ratio of imatinib base to acetone is 1:15 ~30.

4. The preparation method according to claim 1, characterized in that, the molar ratio of imatinib base to methanesulfonic acid is 1:1.0-1.5.

5. The preparation method according to claim 1, characterized in that, the reaction time is 1~36 h.

6. The preparation method according to claim 5, characterized in that, he reaction time is 4~10 h.

7. The preparation method according to claim 1, characterized in that, the method further comprises adding seed crystal of the α-crystal form of imatinib mesylate.

8. The preparation method according to claim 1, characterized in that, the method further comprises the steps of filtering, washing, and drying.

\* \* \* \* \*